United States Patent [19]

Thompson et al.

[11] Patent Number: 5,164,301
[45] Date of Patent: Nov. 17, 1992

[54] PROCESS AND KIT FOR DETECTING MICROBIAL METABOLISM

[75] Inventors: Thomas E. Thompson, Saline; Ruth F. Eden, Ann Arbor, both of Mich.

[73] Assignee: Difco Laboratories, Ann Arbor, Mich.

[21] Appl. No.: 542,115

[22] Filed: Jun. 22, 1990

[51] Int. Cl.$^5$ ............................................. C12Q 1/02
[52] U.S. Cl. .................................. 435/29; 435/4; 435/34; 436/172; 436/800; 250/461.1; 250/461.2
[58] Field of Search ............... 435/34, 29, 4; 436/800, 436/172; 250/461.2, 461.1

[56] References Cited

U.S. PATENT DOCUMENTS

| | | | |
|---|---|---|---|
| 3,564,588 | 2/1971 | Soli | 195/103.5 |
| 3,676,679 | 7/1972 | Waters | 250/83.6 |
| 3,957,583 | 5/1976 | Gibson et al. | 195/103.5 R |
| 4,025,393 | 5/1977 | Hirschfeld | 195/103.5 |
| 4,049,499 | 9/1977 | Lepp et al. | 195/100 |
| 4,116,775 | 9/1978 | Charles et al. | 195/103.5 M |
| 4,118,280 | 10/1978 | Charles et al. | 195/127 |
| 4,221,867 | 9/1980 | McFadden | 435/32 |
| 4,250,266 | 2/1981 | Wade | 195/103.5 |
| 4,311,794 | 1/1982 | Melnick et al. | 435/289 |
| 4,448,534 | 5/1984 | Wertz et al. | 356/435 |
| 4,495,293 | 1/1985 | Shaffar | 436/501 |
| 4,556,636 | 12/1985 | Belly et al. | 435/34 |
| 4,591,554 | 5/1986 | Koumura et al. | 435/18 |
| 4,639,421 | 1/1987 | Sage, Jr. | 435/34 |
| 4,665,024 | 5/1987 | Mansour | 435/34 |
| 4,743,561 | 5/1988 | Shaffer | 435/32 |
| 4,859,584 | 8/1989 | Horan et al. | 435/29 |
| 4,861,709 | 8/1989 | Ulitzur et al. | 435/6 |
| 4,916,060 | 4/1990 | Weaver | 436/800 |

FOREIGN PATENT DOCUMENTS 0070685  1/1983  European Pat. Off.

*Primary Examiner*—Douglas W. Robinson
*Assistant Examiner*—Jane A. Williams
*Attorney, Agent, or Firm*—Reising, Ethington, Barnard, Perry & Milton

[57] ABSTRACT

A process and kit for detecting microbial metabolism is disclosed, the process including the steps of combining medium, a metabolic dye having an absorbance spectrum which in the presence of microorganisms changes and responds to metabolism of the microorganism and a second analytical dye having an excitation or emission spectrum which overlaps with one of the changed or unchanged absorbance spectra of the first dye. The medium contains a sample solution to be analyzed for containing metabolizing microorganisms. The user observes either no change in the fluorescence emissions of the second analytical dye indicating the absence of metabolizing microorganisms in the sample or a change indicating the presence of metabolizing microorganisms in the sample.

18 Claims, 8 Drawing Sheets

PROCESS AND KIT FOR DETECTING MICROBIAL METABOLISM

TECHNICAL FIELD

The present invention relates to a process and kit for detecting microbial metabolism in a fluid sample. More specifically, the present invention utilizes the detection of microbial metabolism to determine the presence of microorganisms in body fluids, foods, water, in bioload and bioburden determinations, as well as for antimicrobial susceptibility testing and microbial identification technology.

BACKGROUND OF THE INVENTION

Detection of the presence of microorganisms, their enumeration, identification, and susceptibility to antimicrobic agents are the main goals of a diagnostic microbiologist. The present invention utilizes a method for detecting microbial metabolism that can be applied to each of these areas.

The early detection of bacteria in body fluids (blood, urine, spinal fluid, abscess exudates) is of paramount importance. The usual method for the detection of bacteria in blood is to inoculate 5 ml of the fluid into a culture medium and wait for the appearance of turbidity which is an indication of bacterial growth. Bottles are inspected daily for turbidity or any other changes indicative of microbial growth. While this method is laborious and slow, it allows for the detection of most organisms. Once an organism is detected, a small aliquot of the organism containing culture media is transferred to a petri dish containing appropriate growth media. The subsequent isolated colonies are used for identification and to test for antibiotic susceptibility.

In the mid nineteen seventies, a radiometric technique for the detection of biological activity in blood was developed. In that method, samples of blood are inoculated into a suitable growth medium that includes a $C^{14}$ containing carbon and energy source. The inoculated medium is incubated for a suitable period and a portion of the gaseous atmosphere is analyzed for $C^{14}O_2$ (U.S. Pat. No. 3,676,679, issued Jul. 1972). A commercial instrument utilizing this technology is available from Becton Dickinson, Johnston Laboratories, 383 Hillen Road, Towson, Mary. 21204. The disadvantages of the system include hazard due to the necessity to handle radioactive material, environmental contamination resulting from multiple entry of the needle through a septum to the sample,s head space, and lack of total automation. More recently a non-radiometric method for the detection of $CO^2$ in the gaseous atmosphere was introduced by Becton Dickinson, eliminating the need to handle radioactive material.

An ideal system for the detection of organisms in body fluids should be totally automated (hands-off), quickly detect the presence of microorganisms, and have non-invasive sampling.

The detection and enumeration of microorganisms in industrial samples (foods, cosmetic, water and pharmaceutical samples, water) has followed a different course of technology. The standard method of analyzing samples is the plate count methodology as shown in Standard Methods for the Examination of Water and Water Waste (1985), 7th Ed. APHA, AWWA, WPCF (PP860-866). By this method, a sample is homogenized and diluted with sterile water. Each decimal dilution of $10^{-1}$ to $10^{-4}$ of the homogenate is poured into a petri dish together with a nutrient medium. The dish is incubated for 24 to 48 hours and the number of colonies on the plate are counted. As an alternative, some laboratories now use automated colony counters. In any event, the standard plate count (SPC) method is extremely time consuming, costly and tedious. Additionally, colony forming units do not always correlate with desired safety parameters being estimated.

A wide variety of alternative techniques have been introduced for faster detection and enumeration of microorganisms in industrial samples including: impedance, conductance, turbidity, CO2, ATP determination etc. Impedance and conductance methods measure changes in the electrical properties of the growth media as a result of bacterial metabolism. Both impedance and conductance lend themselves to full automation and result in much faster detection of microorganisms than is possible with the SPC methodology. The limitations of these methodologies include sensitivity of the signal to stray electrical interference, sensitivity to temperature fluctuations, no visible back up to assure that the data is accurate and as a result false positives may be often encountered.

In the turbidity method, the time required to obtain a certain absorbance is recorded. Growth curves are derived. The disadvantages of the system include interference due to turbid material in the samples resulting in the need for dilutions. The method tends to be slower than impedance but faster than SPC.

The ideal system should be fully automated, quickly detect and enumerate microorganisms, and possess a visual backup capability.

The most common techniques for bacterial identification relate to the organism's biochemical properties. Each organism possesses a unique set of enzymes. By performing a series of chemical reactions in growth media, organisms can be identified by a combination of positive and negative reactions that effectively provide a biochemical fingerprinting of the organisms.

Typical identification reactions include carbohydrate fermentation, utilization of substrates such as citrate and urea, production of hydrogen sulfide, indole, lysine decarboxylase etc. or inhibition resulting from antimicrobic agents. A reaction result is determined by a visual color change in the medium or by the presence of turbidity.

The color reagent in most cases is a pH indicator which measures the alkalinity or acidity resulting from the chemical reactions. Another mechanism for color development is the enzymatic splitting of chromogens. A number of manual systems such as API20 (Analytab Products, Plain View, N.Y.), EnterotubeII (Roche Diagnostis, Nutly, NJ), Minitek (BBL Microbiological systems, Cockeysville, MD) are based on this principle.

The positive and negative tests generate a profile number which can be correlated to an organism identification by use of the systems data base. The results are usually available in 12-18 hours and a significant amount of manual manipulation is required.

The trend over the last ten years has been toward automation of these tests to reduce hands on technical time and in some instances to decrease the time for obtaining results. The Autobac IDS system (General Diagnostics, Morris Plains, N.J.) is a semi-automated system and measures microbial growth by light scattering at a fixed 35 angle (U.S. Pat. No. RE28,801). The Automicrobic System (Vitek System, Inc., Hazelwood, Mo.) is a fully automated system (Gibson et al U.S. Pat. No. 3,957,583; Charles et al U.S. Pat. No. 4,118,280; and Charles et al U.S. Pat. No. 4,116,775). The bacterial suspension is drawn into small wells of a card cuvette. The cards are inserted into the machine that monitors changes in optical absorbance. The card is moved automatically into the sensing slot and is monitored every 30 minutes. The Avantage Microbiology Center (Abbott Laboratories, Irving, TX) uses changes in optical density or turbidity. American MicroScan (Baxter Health Care Corp., West Sacramento, Calif.) has an automated system that scans each well of a multi-well tray containing many liquid-based fluorescent assays. A single light source is passed through the wells. Each well's fluorescence is read in sequence. The resulting fluorescence intensity information is transferred to a computer for interpretation using probabalistic methods (U.S. Pat. No. 4,448,534).

The preferred system for the identification of microorganisms should be fully automated, identify quickly (2-3 hours), have a color read visual backup and allow for simple inoculation.

The traditional method used for testing antimicrobial susceptibility has been the standardized disk diffusion method described by Kirby and Bauer (Bauer, Kirby et al. 1966, American J. Clinical Pathol., Vol. 45 (4), p493). According to this method and subsequent modification, colonies are picked and suspended in liquid to result a predetermined turbidity, and streaked onto a nutrient agar in a petri dish. Paper disks impregnated with different anti-microbial material are placed on the inoculated agar surface, and the drug is allowed to diffuse through the agar, forming a gradient around the paper disk. As bacteria grow, they form a visible film on the agar surface. However, around the antibiotic impregnated disks, growth is inhibited if the organism is susceptible to the agent. The zone of the inhibition around the disk is proportional to the degree of susceptibility. The disadvantages of the method are the long incubation time required (18 hours), lack of standardization, and lack of quantitation.

A more common method for antimicrobic susceptibility is minimal inhibitory concentration (MIC). The MIC is determined by making serial dilutions of the drug in a nutrient broth, and inoculating each dilution with a standardized suspension of bacteria. After incubation the various dilutions are examined for turbidity. The MIC is defined as the lowest antibiotic concentration that inhibits macroscopic growth of the test organism. Trays of microtubes are commercially available with frozen or dry solutions of various antibiotics such as those offered by Micro-Media Systems (Potomac, Md.); MicroScan (Baxter Healthcare, W. Sacramento, Calif.); Pasco Laboratories (Wheat Ridge, Co.), Sceptor (BBL, Houston, Tex.). These trays are manually inoculated, incubated for 16-18 hours and often manually read.

The same automated systems used for the identification of microorganisms are also used for MIC detection.

The present invention utilizes fluorescence techniques to achieve a quick, efficient and sensitive means for detecting the presence of microbes, enumerating and identifying microbes, and testing antimicrobial susceptibility of microbes.

Fluorescence is attractive as a detection method due to its inherent sensitivity. The lower limits of detection are in the range of a few thousandths to a tenth of a part per million. A small number of microorganisms can be rapidly detected by means of fluorescence analysis. Koumura et al 1986 (U.S. Pat. No. 4,591,554) used specific umbelliferon derivatives such as 4-methylumbelliferyl phosphate and 4-methyl umbelliferyl galactoside to determine the sanitary quality of various kinds of foods, beverages, water and toilet articles. Sensititer (Gibco Laboratories, Andover, MA) uses fluorescent substrates (such as umbelliferons and coumarin drivatives) that are non-fluorescent until acted on by microorganisms. American MicroScan (Baxter Health Care Corp., West Sacramento, Calif.) uses a series of fluorogenic substrates and indicators consisting of 4-methylumbelliferyl compounds and 7-amido-4-methylcoumarin compounds to rapidly identify microorganisms (2-4 hours) and for rapid determination of their antimicrobic patterns (6-8 hours).

The U.S. Pat. No. 4,495,293 to Shaffar, issued Jan. 22, 1985 discloses a method for fluorometrically determining a ligand in an assay solution wherein the intensity of the fluorescence emitted by the assay solution is related to the change in the transmittance properties produced by the interaction of the ligand to be determined and a reagent system capable of producing a change in the transmittance properties of the assay solution in the presence of the ligand. This is an example of a two dye system wherein one dye in the reagent system interacts with a specific ligand. The interacting dye has an optical spectrum which changes upon interaction with the ligand thereby effecting the fluorescence emission from a second dye. The process thereby measures the presence and amount of the ligand in the sample at dye concentrations that may be toxic to life forms but are effective at measuring ligands.

The present invention utilizes a two dye fluorescence emission system which does not detect or measure a ligand but rather allows or detects microbial growth and utilizes this information for the detection, enumeration, identification, and susceptibility testing of the microorganisms.

SUMMARY OF THE INVENTION

In accordance with the present invention, there is provided a process for detecting microbial metabolism including the steps of combining growth medium, a first dye having an absorbance spectrum which in the presence of microorganisms changes in response to metabolism of the microorganism, and a second fluorescent dye having an excitation and/or emission spectrum which overlaps with one of the changed or unchanged absorbance spectra of the first dye, the growth medium containing a sample solution to be analyzed for containing metabolizing microorganisms. The fluorescence emission of the second dye is observed as to either not changing to indicate the absence of metabolizing microorganisms in the sample or changing to indicate the presence of metabolizing microorganisms in the sample.

The present invention further provides a kit for detecting microbial metabolism, the kit including growth medium, a first dye having an absorbance spectrum in the presence of microorganisms which changes in response to metabolism of the microorganisms and a second fluorescent dye having an excitation and/or emission spectrum which overlaps with one of the unchanged or changed absorbance spectra of the first dye. Addition of the first and second dyes to the growth medium without metabolizing microorganisms causes no change in the observed fluorescence emission of the second dye. Addition of the first and second dyes to growth medium containing microorganisms causes changes in the observed fluorescence emission of the second dye.

FIGURES IN THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
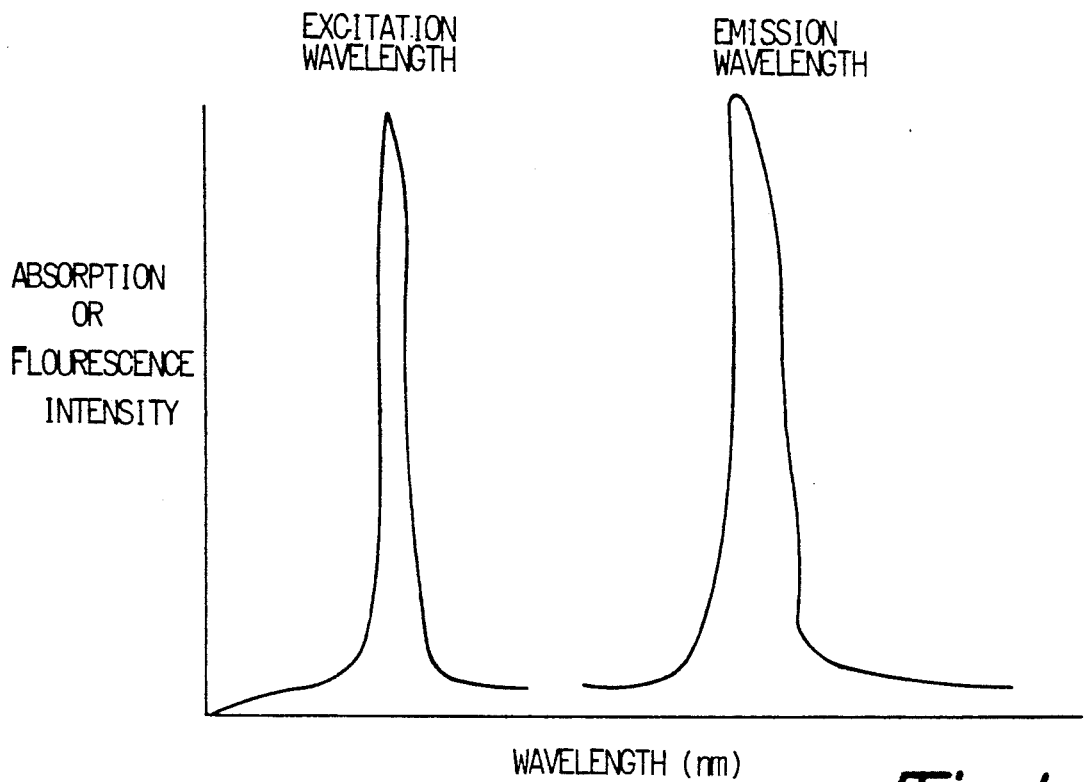
FIG. 1 is a graph of absorption or fluorescence intensity versus wavelength of an analytical fluorescent dye which is quenched by the presence of a metabolic dye having an absorbance spectrum which overlaps the emission spectrum of the analytical dye.

A process for detecting microbial metabolism in accordance with the present invention generally includes the steps of combining growth medium, a first dye (metabolic dye) having an absorbance spectrum which in the presence of microorganisms changes in response to metabolism of the microorganism, and a second fluorescent dye (analytical dye) having an excitation and/or emission spectrum which overlaps with one of the changed or unchanged absorbance spectra of the first dye, the growth medium containing a sample solution to be analyzed for containing metabolizing microorganisms. The combined solution is observed as to either emitting no change in the fluorescence emission of the analytical dye indicating the absence of metabolizing microorganisms in the sample or a change in the emission of the analytical dye indicating the presence of metabolizing microorganisms in the sample. It is this ability of the present invention to detect metabolizing microorganisms in samples and the direct relationships of microorganism metabolism to growth that lends the present invention for use in microbial detection, enumeration, identification, and antimicrobial susceptibility testing. That is, the present invention generally provides the capability of combining the increased precision of fluorescence detection with the increased speed of monitoring microorganism growth by monitoring microorganism metabolism that provides the present invention with advantages over the prior art.

The medium is chosen to promote the growth of the microorganisms being tested. The medium may simply contain carbohydrates. Or, for example, a growth medium capable of promoting the growth of a wide spectrum of microorganisms may be used for microbial detection and enumeration tests where a fluid sample is obtained from a patient and the identity and number of the microorganism is not known. On the other hand, if a particular microorganism of known identity is being tested, then the growth medium can be selected to promote the growth of that microorganism. That is, if the microorganism requires specific nutrients to promote their growth, then the growth medium can be selected to include those nutrients. Examples of growth medium that can be utilized with the present invention are Mueller-Hinton, Colombia broth, Brain heart infusion, tryptic soy broth, Schaedlers broth.

The metabolic dye is chosen such that its spectral properties respond to biochemical changes to its physical chemical environment. That is, microbial metabolism can change the physical chemical environment of the metabolic dye as the microorganisms metabolize nutrients from the medium and shift the absorbance spectrum of the first dye. This results in quenching or unquenching of the emission spectrum of the analytical dye. The investigator would then observe the quenching or unquenching of the fluorescence emission of the analytical dye indicating the presence or absence of metabolizing microorganisms.

If the growth medium contains specific nutrients which change the physical chemical properties of the growth medium when metabolized by specific microorganisms, the changing of the physical chemical environment of the metabolic dye can be indicative of metabolizing of a specific type of microorganism and the observed change in emission of the analytical dye used and an identification of the specific type of microorganism results. Alternatively, several different media containing different specific nutrients can be utilized. The combined samples would be observed for changes or absence of changes of the emission of the analytical dye and an identification finger print can be constructed of specific microorganisms based on the several observations.

The physical chemical environment of the metabolic dye can be changed by the changing of the pH of the media. The metabolic dye would be chosen as having an absorbance spectrum which changes in response to changes in the pH of the environment. Bromthymol blue is an example of a dye which changes its absorbance spectrum in response to pH. Bromthymol blue has proven effective in commercially available identification systems previously developed. Bromcresyl purple can also be used. Both dyes are freely water soluble, nontoxic at effective concentrations, have a pKa near neutrality, have a high extinction coefficient, are inexpensive, have a visual color change, have a good overlap with preferred analytical dyes, and have been shown to function in accordance with the present invention for a rapid identification test. Examples of other pH indicator compounds that are suitable are phenol red and chlorophenol red.

An example of microorganism metabolism which change pH are the addition of specific carbohydrates to the growth media which are fermented to acidic end products by certain microorganisms. The acidic end products change the pH of the growth medium. Alternatively, urea can be added to the growth medium which is enzymatically transformed by microorganisms containing urease to ammonia. The ammonia produced raises the pH of the environment.

The physical chemical environment of the metabolic dye can also be changed by changing the reduction-oxidation potential of the environment, the first dye having an absorbance spectrum which changes in response to changes in the reduction oxidation potential of the environment. Examples of metabolic dyes which are sensitive redox potential indicators are: resazurin, thionin, methylene blue, dichlorophenol indophenol, neutral red, indigo carmine, N,N dimethylindoaniline.

Resazurin can be used because it is inexpensive, insensitive to thermal and light degradation, water soluble, has high extinction coefficient, has a visible, distinct color change upon reduction, is reduced by most or all microorganisms, and has good spectral overlap with preferred analytical dyes discussed below. Resazurin does not appear to effect the function of normal antibiotics, and it is therefore excellent for use in MIC determinations.

Certain metabolic dyes can be chosen as enzymatic cleavage substrates. For example, indoxyl and bromo-chloro-indoyl compounds can be chosen as enzymatic cleavage substrates for the same reasons as described for the metabolic dyes uses as pH indicators. Rather than having a useful pKa, these dyes possess the ability to be colorless when chemically linked to a compound and colored when they have been cleaved and are free in solution. This property allows these metabolic dyes to go from a nonquenching state to a quenching state upon cleavage of the linking bond.

The analytical dye is chosen from a wide variety of fluorescent compounds. Examples of analytical dyes are sulforhodamine 101, rhodamine B, rhodamine 6, flouroscein, and eosin Y. Sulforhodamine (SR101) has been preferred as the fluorescent dye because it is water soluble, has excitation and emission wavelength different from resazurin fluorescence (resazurin being one of the preferred metabolic dyes), it is relatively inexpensive, and it has an excitation and emission spectra that overlaps with resazurin, bromcresyl purple, bromthymol blue, indoxyl, and bromo-chloro indoyl. SR101 also has good quantum yield, is nontoxic to microorganisms at the current concentrations utilized in accordance with the present invention, and is quite stable to temperature and light challenge. The compound has been dried to complete dryness at 42.C without loss of fluorescence. SR 101 also has a reasonable Stokes shift. The excitation and emission wavelengths are in the visible range, allowing the use of inexpensive glass and plastic containers for emission observation, rather than UV transparent materials for the system is disposable cuvettes and instrument windows.

The analytical dye is chosen such that either excitation, emission, or both excitation and emission wavelengths coincide or overlap with the absorbance spectrum of the metabolic dye. The overlap can be either of the metabolized or unmetabolized form of the metabolic dye, but must not overlap both. It is this specific combination of properties of the metabolic dye and analytical dye which characterize the present invention. Moreover, as discussed below, it is the ability of these dyes to cooperate in accordance with the present invention without being toxic to the microbes being analyzed that further characterize the present invention.

The overlap of spectrum of the two dyes can either be of the metabolized or unmetabolized form of the metabolic dye, there cannot be any of overlap of both dyes.

Figure 2:
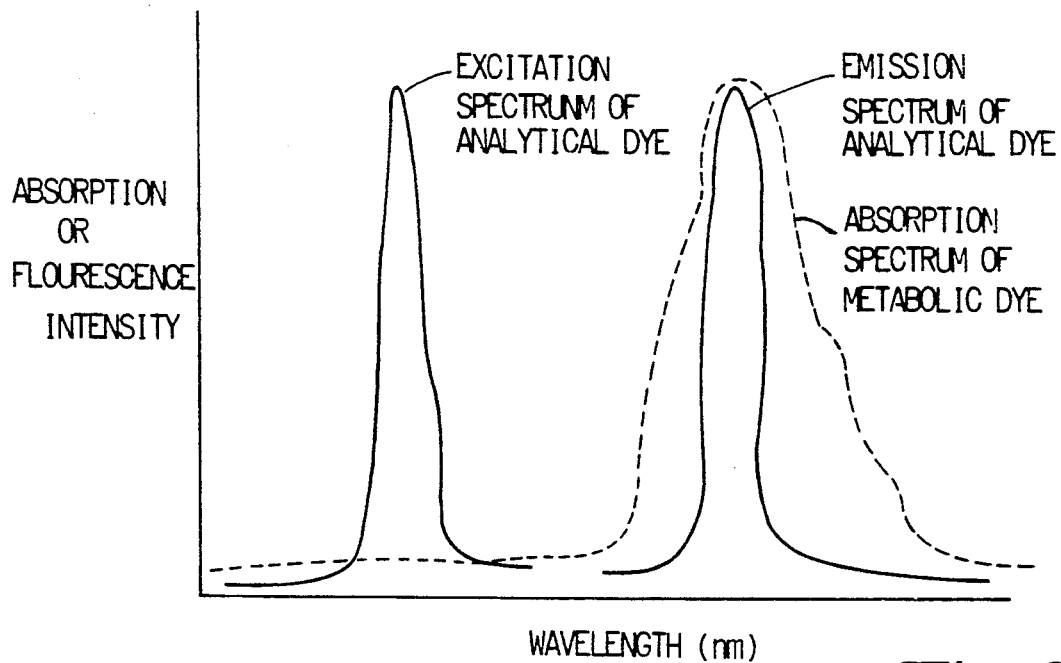
FIG. 2 is a graph of absorption or fluorescence intensity versus wavelength of an example of an analytical dye whose emission spectrum overlaps the absorbance spectrum of a metabolic dye.
Figure 3:
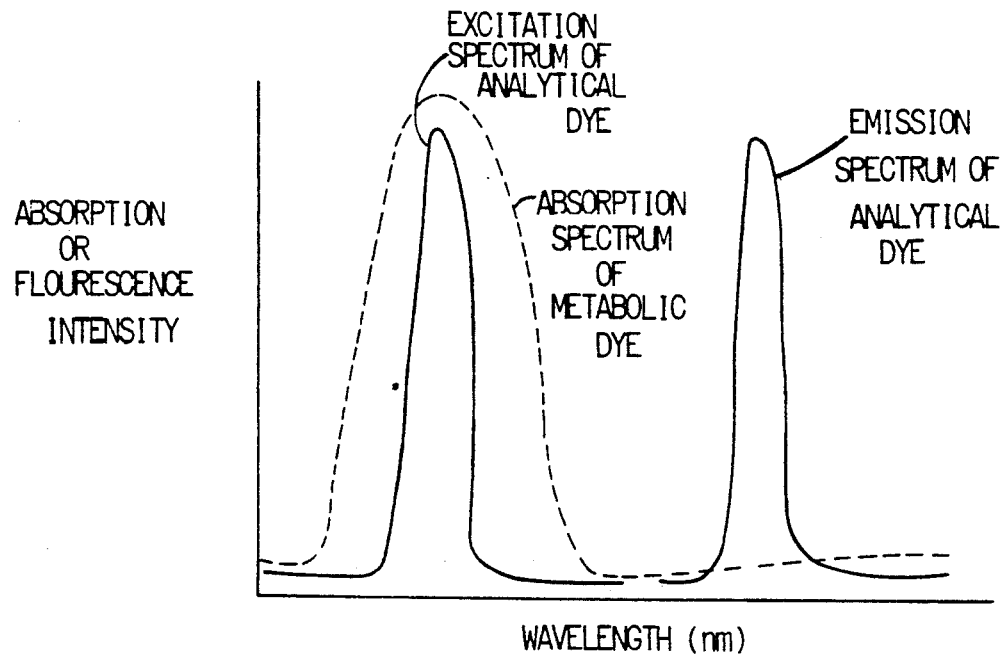
FIG. 3 is a graph of absorption or fluorescence intensity versus wavelength of an example of an analytical dye whose excitation spectrum overlaps that of the metabolic dye.
Figure 4:
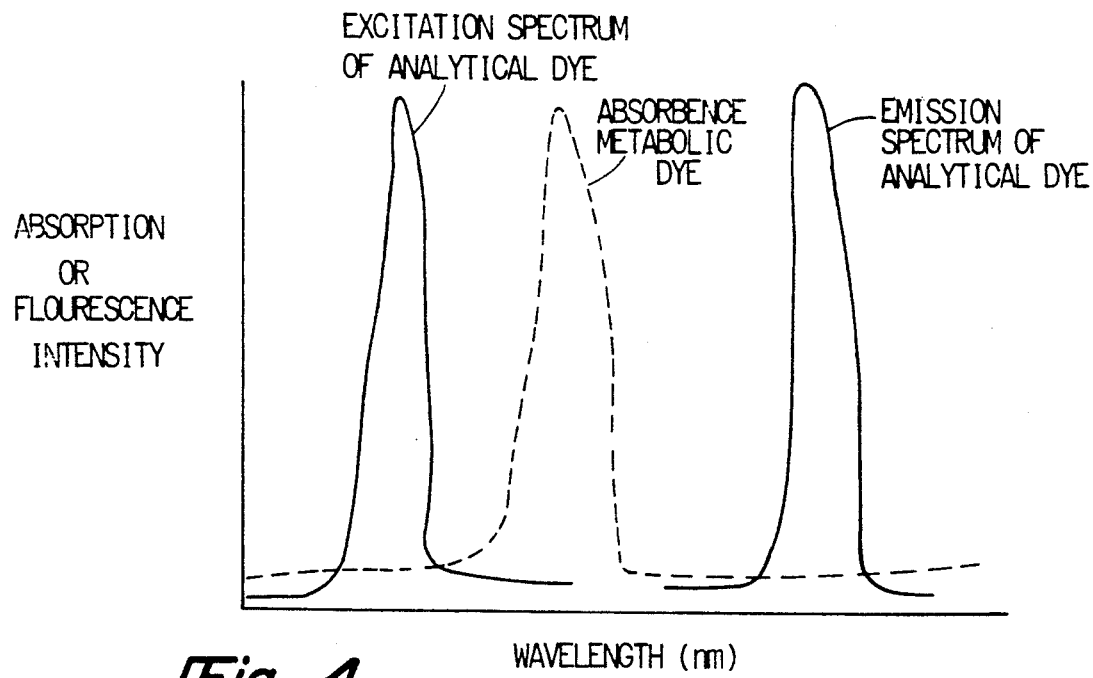
FIG. 4 is a graph of absorption or fluorescence intensity versus wavelength of a metabolic dye spectrum which does not overlap significantly with the fluorescence spectrum of the analytical dye.

A hypothetical example of an analytical dye whose emission spectrum overlaps the absorbencies of the metabolic dye is shown in FIG. 2. A hypothetical example of an analytical dye whose excitation spectrum overlaps that of the metabolic dye is shown in FIG. 3. In either of these two hypothetical examples the measured fluorescence of the analytical dye would be less than that in the absence of the metabolic dye as shown in FIG. 1. That is, the analytical dye fluorescence is quenched by the presence of the metabolic dye in the overlap condition. If the metabolic dye spectrum does not overlap significantly with the analytical dye as shown in FIG. 4, the fluorescence of this system is as high as that of the analytical dye. This is the unquenched situation.

In practice, a test sample containing microorganisms is introduced into a well containing the appropriate growth medium as discussed above, along with an analytical dye, and a metabolic dye. The well containing the mixture is placed in an incubator at growth temperature (about 30° to 35° C. per human pathogens) and fluorescence is monitored over a two to eight hour period.

Each of the graphs showing increases in fluorescence over time in the Figures of the present application show an initial lag time (initial flat phase of the curve) which has been determined to be dependent upon the level of organisms in the sample. That is, the length of the lag time is directly proportional to the number of organisms in the sample such that, for particular organisms, a standard curve can be constructed. The time period of the lag period is observed as an indication of the number of microorganisms in the medium. Thusly, the present invention can be used to enumerate microorganisms in a test sample.

After the initial lag time, dependent upon the level of the microorganisms in the sample as discussed above, the fluorescence rapidly increases when microorganisms are present. The onset of the acceleration is referred to herein as the detection point. If bacteria are not present in the system, the fluorescence curve may drift slightly but will never accelerate and reach the high fluorescence levels attained with the presence of bacteria. Accordingly, observation of the detection point is an immediate notice of the presence of microorganisms in the sample. One need not wait for the presence of sufficient growth of the microorganisms to effect turbidity of a sample to indicate microbe presence as in prior art tests, but rather one need only wait for sufficient metabolism by the microbes to effect the environment of the metabolic dye thereby causing a shift in the optical spectrum in the metabolic dye and thereby quenching or unquenching the fluorescence emission of the analytical dye to determine the presence of bacteria in a sample. This can be accomplished within two to eight hours as opposed to the significantly longer periods of time required by prior art methods.

Microbial susceptibility or resistance to an antibiotic can be tested by adding increasing concentrations of an antibiotic to different samples of growth medium containing microorganisms. The inventive method is performed in accordance with the present invention and the lowest concentration of antibiotic capable of preventing a change in the fluorescence emission of the analytical dyes observed as indicating sensitivity of the microorganisms to the antibiotic. Alternatively, different antibiotics can be added to different samples of the growth medium containing the microorganism. In this situation, antibiotics which prevent a change in the fluorescence emission or cause a change in the fluorescence emission of the analytical dye can be observed as indicating sensitivity of a microorganism to particular antibiotics.

As mentioned above, the concentrations of the metabolic dye, the analytical dye, and any other reagent utilized in the assay, has to be nontoxic to microorganisms allowing their growth and metabolism. For example, the U.S. Pat. No. 4,743,561 to Schaffer, issued May 10, 1988, discloses the use of a two-dye system for detecting the concentration of a ligand in a test sample. All their assays include toxic reagents that will prevent the metabolism and growth of microorganisms. For example, they utilize a variety of chemicals that are strong disinfectants and germicides, all of which will kill most microorganisms upon contact such as: hydrogen peroxide, formaldehyde, phenol, potassium cyanide, potassium hydroxide, potassium thiocyanate, 8-quinolinol sulfate, mercuric chloride, thimersol, etc. Their assays utilize strong acids (sulfuric acid, sulfamic acid) or bases (sodium hydroxide) yielding pHs which will prevent any microbial metabolism. Likewise, other prior art information discloses dye systems wherein the dye, per se, would kill or inhibit the microbes and thereby obviate the usefulness of the present invention. The present invention does not measure the presence of a ligand, but rather metabolic activity of microorganisms and only utilize metabolic and analytical dyes which do not inhibit microorganism growth.

A kit can be provided in accordance with the present invention for detecting microbial metabolism and utilizing this method for microbial identification, detection, enumeration, and susceptibility testing. The kit would include growth medium, the first dye having an absorbance spectrum which in the presence of microorganisms changes in response to metabolism to the microorganisms and a second fluorescent dye having an excitation or emission spectrum which overlaps with one of the unchanged or changed absorbance spectra of the first dye whereby addition of the first and second dyes to the growth medium without metabolizing microorganisms causes no change in the observed fluorescence emission of the second dye and with metabolizing organisms causes changes in the observed fluorescence of the emission of the second dye.

The following is a practical example of the quenching/unquenching of the fluorescence of the dye pair system chosen in accordance with the present invention as it respond to its environment. The addition of a small amount of sodium dithionite to a SR101/resazurin solution causes the fluorescence to increase significantly, as the blue quenching resazurin is reduced to the red resorufin or colorless dihydroresorufin compound. These compounds will not quench SR 101 fluorescence. The same phenomenon is shown with the pH sensitive indicators bromthymol blue and bromcresyl purple. At high pH, (greater than 7.5), the blue indicator quenches the fluorescence of SR 101. At lower pH, (less than 6.5), the yellow colored dye forms do not quench. Thus, the environment can be shown to effect the overall fluorescence detected from the dye pair solution.

The following are specific examples of the present invention as used for microbial detection, enumeration, identification, and sensitivity testing.

EXAMPLES

Example 1:

Effect of pH and redox potential on fluorescence with the dye pair

A mixture of 10um Sulforhodamine 101 (SR101) and 20uM resazurin in 100 ul water was prepared. The initial fluorescence (excitation=586 nm, emission =607 nm) was read in microtiter trays using a Flow Fluoroscan II fluorometer. A small amount of sodium dithionite was added to reduce the resazurin from the initial blue color to pink. The fluorescence rises dramatically (Table 1) showing a response to the immediate redox environment. Replacing the resazurin with bromthymol blue or bromcresol purple and altering the pH of the solution demonstrates a response of the dye pair system to pH (Table 1).

TABLE 1

|  | Fluorescent Units | pH |
|---|---|---|
| SR101/Resazurin oxidized (blue) | 4,676 | 7.21 |
| SR101/Resazurin partially reduced (bluish-pink) | 6,697 | 7.22 |
| SR101/Resazurin reduced (clear) | 16,204 | 7.19 |
| SR101/Bromthymol blue (blue) | 2,311 | 7.2 |
| SR101/Bromthymol blue (yellow) | 18,124 | 5.6 |
| SR101/Bromcresol Purple (purple) | 2,260 | 7.2 |
| SR101/Bromcresol Purple (yellow) | 16,169 | 4.9 |

Example 2

Detection of presence of microorganisms and estimating of their numbers

Figure 5:
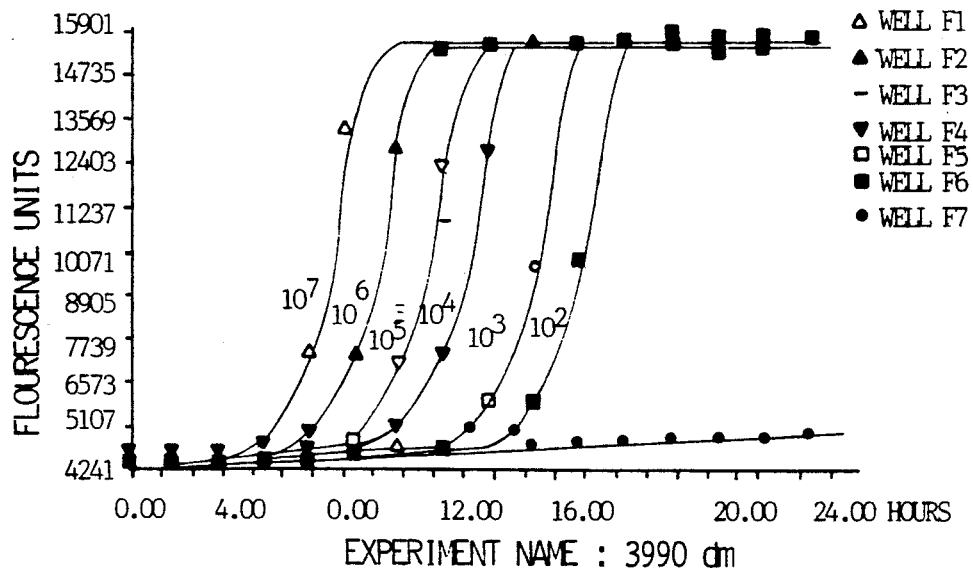
FIG. 5 is a graph of fluorescence units versus time for samples including decreasing numbers of bacteria in growth medium and including an analytical dye and a metabolic dye in accordance with the present invention, the cultures being incubated and read at intervals, the bacteria being *Pseudomonas aeruginosa*.
Figure 6:
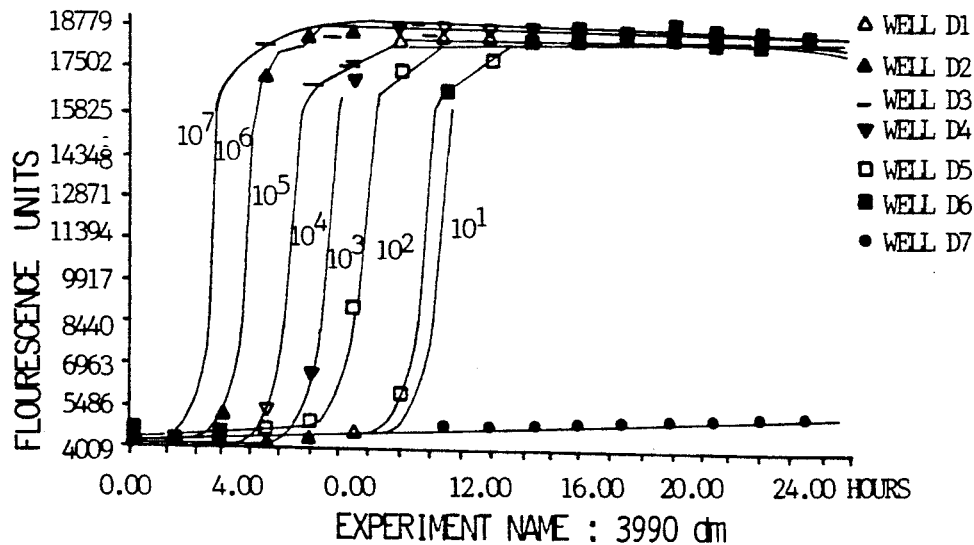
FIG. 6 is a graph of fluorescence units versus time for samples including decreasing numbers of bacteria in growth medium and including an analytical dye and a metabolic dye in accordance with the present invention, the cultures being incubated and read at intervals, the bacteria being *Escherichia coli*.

The method of the present invention can detect growth of bacteria. SR101 (10 uM) and resazurin (20 uM) are added to Mueller Hinton broth (Difco). The medium is seeded with an inoculum of decreasing numbers of bacteria. 100 ul of the seeded broth cultures are placed in wells of microtiter trays, incubated at 35.C, and read at intervals with the instrumentation describe in Example 1. FIGS. 5 and 6 are curves generated when the seed bacteria are *Pseudomonas aeruginosa* and *Escherichia coli* respectively. After an initial lag period that is dependent on inoculum cell number, the fluorescence rapidly increases to a plateau as the resazurin is reduced from blue to the pink (resorufin) or colorless by the metabolism of the growing bacteria. $10^7$ *E. coli* cells generate a signal in two hours under these conditions, while 10 cells can be detected in as little as 10 hours. If bacteria are not present in the system no significant increase in fluorescence is observed.

Figure 7:
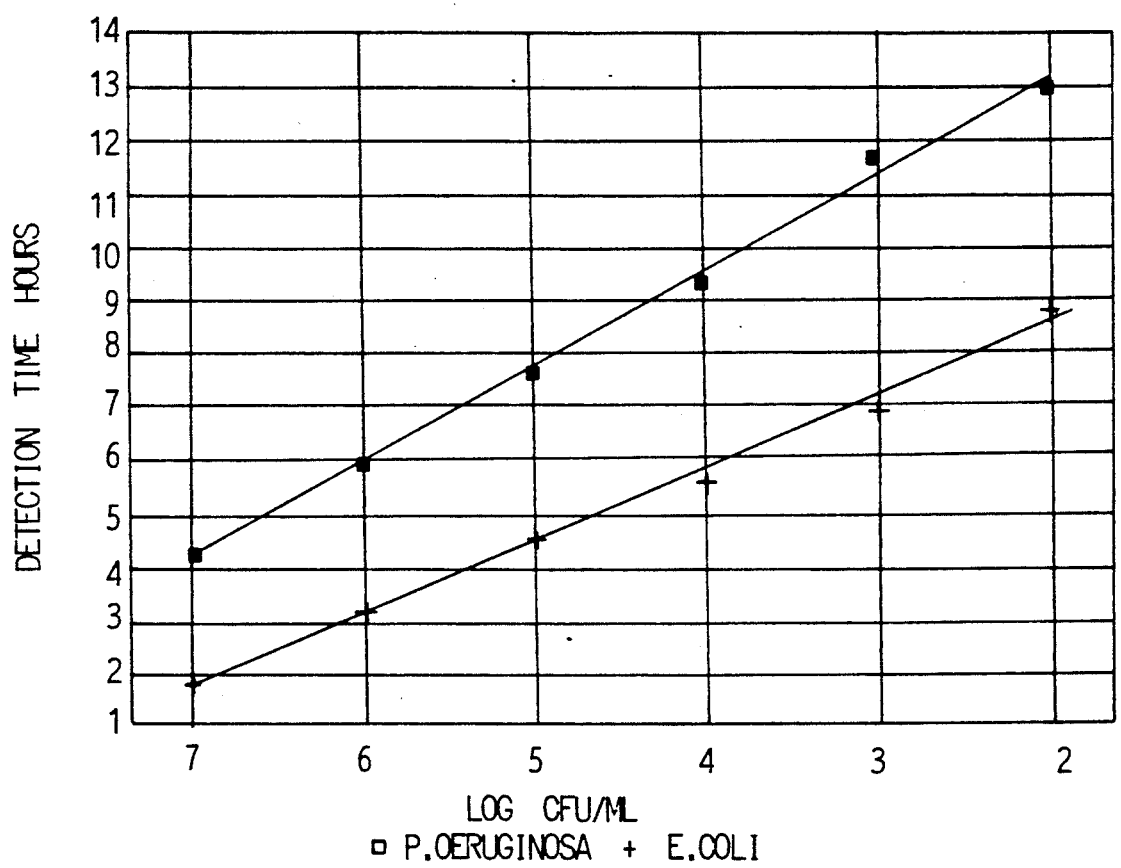
FIG. 7 is a graph of fluorescence detection time in hours versus log colony forming units per ml presenting a calibration curve which can be used to accomplish bacterial enumeration.

Bacterial enumeration can be accomplished by generating a calibration curve similar to the one shown in FIG. 7. The detection time (time required to reach the acceleration point) is correlated to the numbers of colony forming units per ml obtained by a plate count methodology. From this calibration curve the numbers of organisms in the sample can be derived.

Example 3

Detection and enumeration of bacteria in food

Figure 8:
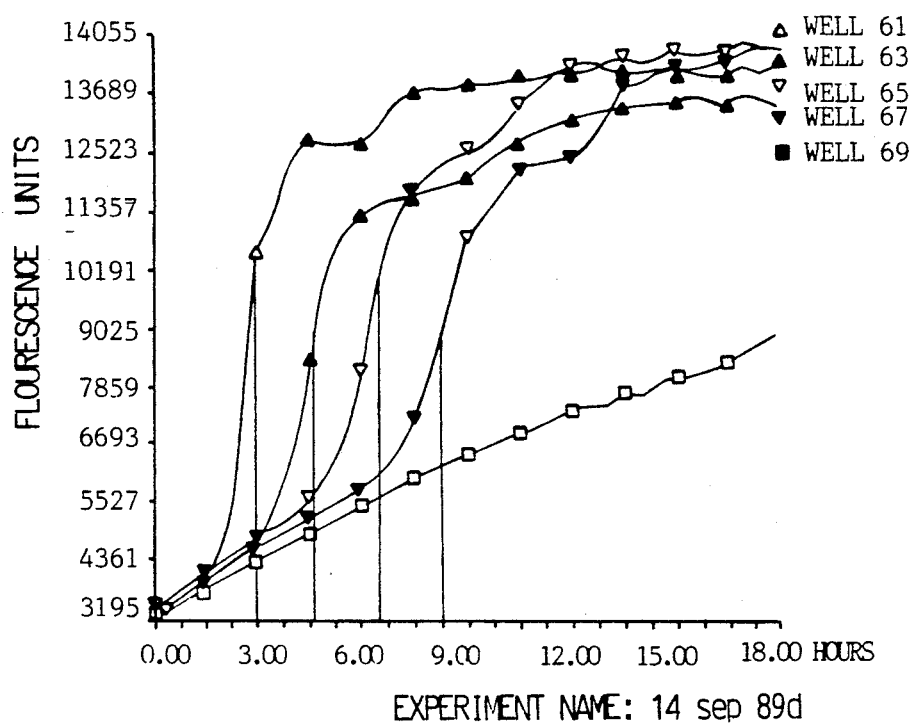
FIg. 8 is a graph of fluorescent units versus time demonstrating detection and enumeration of bacteria in fold namely black pepper.
Figure 9:
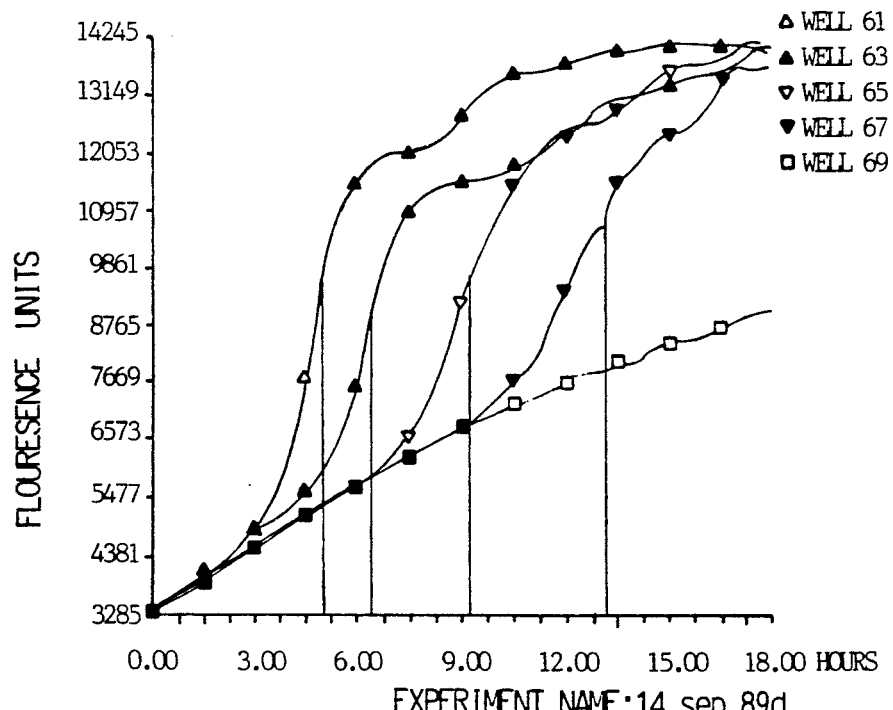
FIG. 9 is a graph of fluorescent units versus time demonstrating detection and enumeration of bacteria in food, namely hamburger.

One hundred grams of food was added to Brain Heart Infusion (BHI) broth (Difco), seeded with approximately $10^7$ cfu/ml of *Escherichia coli* and blended using a Tekmar food stomacher. Black pepper and raw hamburger were tested. 10 uM SR101 and 20 uM resazurin were added to the BHI broth before stomaching. 100 ul samples of the resultant suspension were diluted and placed in wells of microtiter trays and the fluorescence followed over time. The food has significant reducing capability, as can be seen by the increased background slope. Again, the less diluted samples generated earlier detection times, as evidenced by the rapid rise in fluorescence over the background range (FIGS. 8 and 9). Microbically contaminated foods can therefore be detected by following the increase in fluorescence, the faster appearing the acceleration point (shorter lag period) indicative of more bacteria present in the system.

Example 4

Detection of bacteria in blood.

Figure 10A:
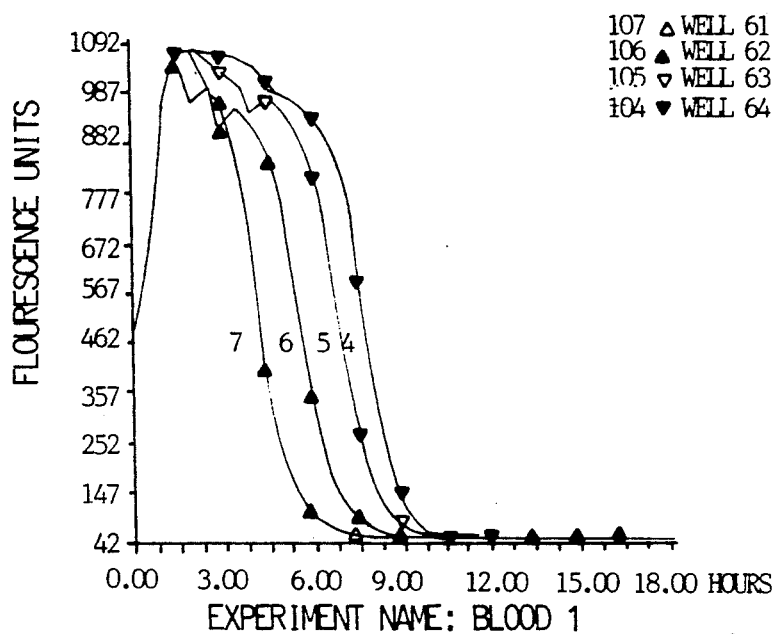
FIG. 10A and 10B shows two graphs of fluorescent units versus time demonstrating the detection of bacteria in blood samples.
Figure 10B:
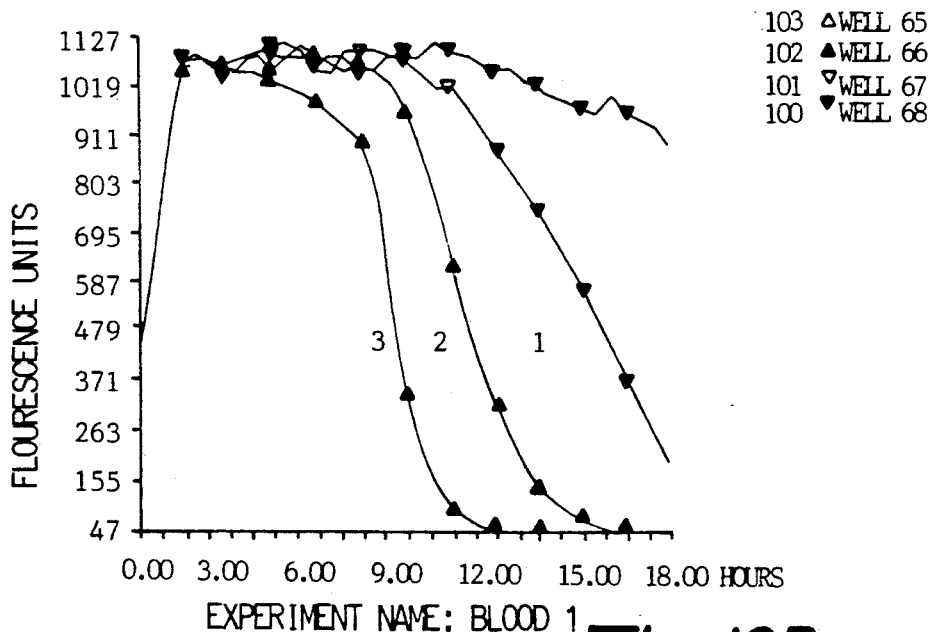

An experiment to determine whether the dye pair system could be used to detect the presence of bacteria in blood (bacteremia) was performed. 10% sterile sheep red blood cells were prepared in Columbia broth (Difco). Resazurin (20 uM) and SR101 (10 uM) were added, and the broth was seeded with *Staphylococcus aureus* at various concentrations. 100 ul of each suspension was placed in microtiter plates and the fluorescence followed as before. Interestingly, the growth of the organism causes a decrease in fluorescence, as opposed to the earlier examples. 100 and 10 bacteria per ml were detected in approximately 10 and 12 hours respectively in this system (FIG. 10).

Example 5

Antimicrobial susceptibility testing.

Figure 11:
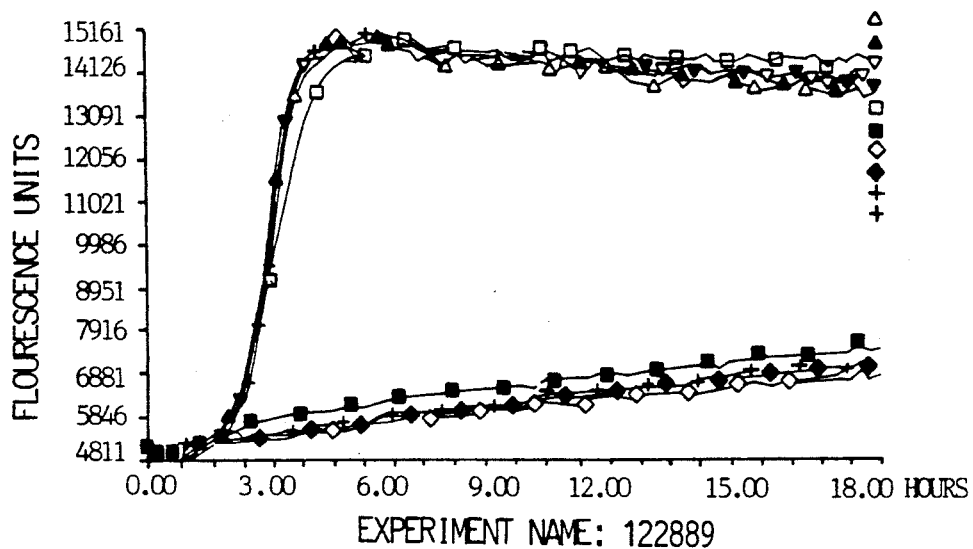
FIG. 11 is a graph of fluorescent units versus time showing a test of antimicrobial susceptibility.

Mueller Hinton broth containing 10 uM SR101 and 20 uM resazurin was prepared. Additions of doubling dilutions of the antibiotic pencillin from 0.0625 to 16 ug/ml were made. 100 ul aliquots of these solutions were placed in microtiter tray wells and inoculated with *Enterococccus faecalis* at $10^6$ cfu/ml. Parallel control panels with the same antibiotics and organism, but no SR101 or resazurin were also set up. The dye containing panels were followed via fluorescence (FIG. 11). The other panel was read using visible turbidity at 18 hours as a measurement of growth. The penicillin Minimal Inhibitory Concentration, or MIC, was found to be 2 ug/ml for both the dye pair and turbidometric systems. The MIC is the lowest antibiotic concentration that inhibits macroscopic growth of the test organism, and is a measure of the sensitivity of the strain to the particular antibiotic. In the fluorometric determination (FIG. 10), the fluorescence in wells that grow parallel that of the no penicillin positive control, while inhibited wells show no significant fluorescence increase over the test period. The penicillin MIC for this organism could be determined as early as three hours using the dye pair technique.

Example 6

Identification of bacteria.

Figure 12:
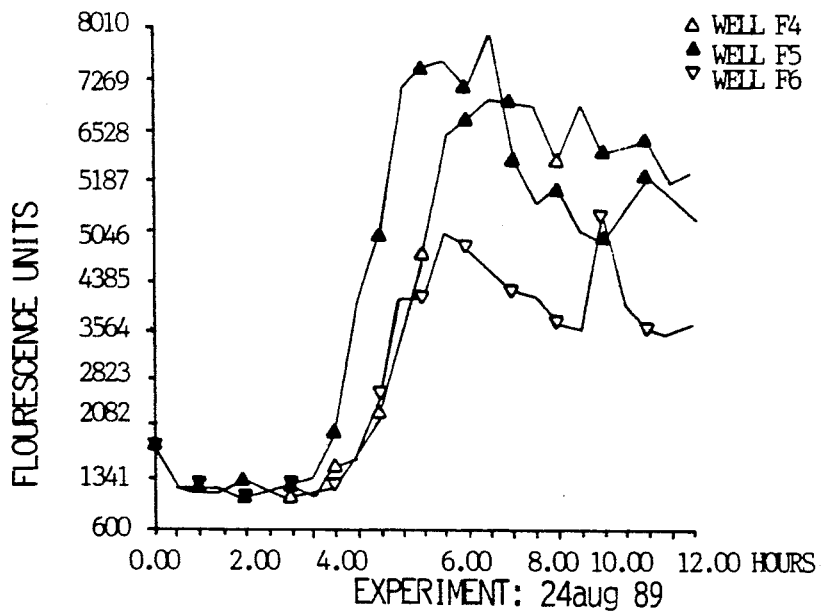
FIG. 12 is a graph of fluorescent units versus time showing the use of the present invention for the identification of bacteria, namely *Enterococcus faecalis*.
Figure 13:
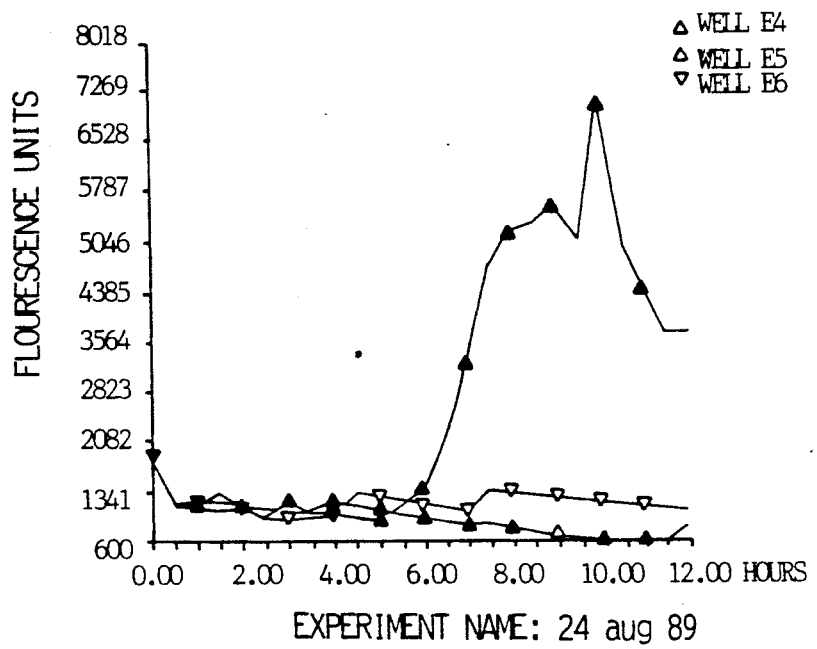
FIGS. 13 is a graph of fluorescent units versus time showing the use of the present invention for the identification of bacteria, namely *Steptococcus agalactiae*.
Figure 14:
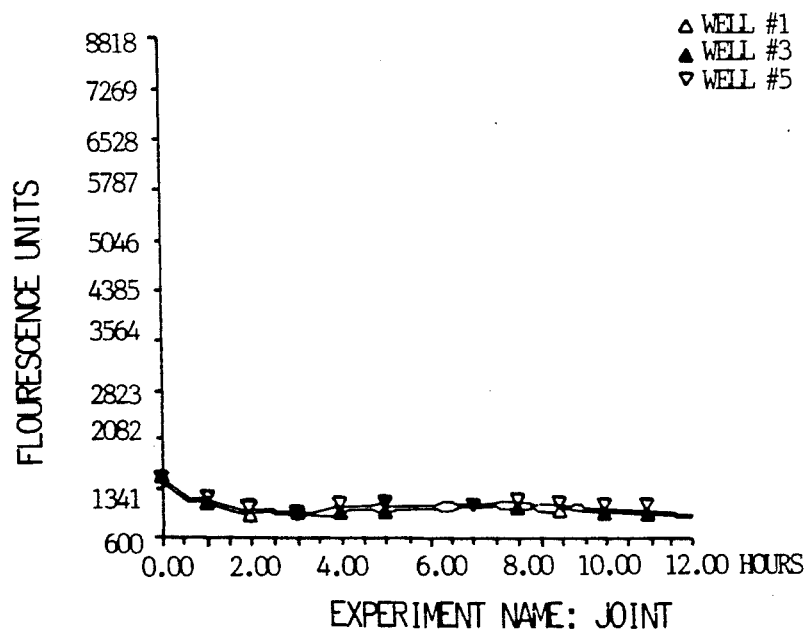
FIG. 14 is a graph of fluorescent units versus time showing the use of the present invention for the identification of bacteria, namely *Staphylococcus epidermidis*.

The use of the dye pair system in identification of unknown bacteria was examined. Heart Infusion broth (Difco) (pH 7.4) was supplemented with 1% wt/vol of one of three carbohydrates, trehalose, mannitol, or mannose. The medium also contained 10 uM SR101 and 24 uM bromcresyl purple. The carbohydrate broths were pipetted into microtiter tray wells (100 ul/well), inoculated with $10^6$ cfu/ml of pure cultures of bacteria, and the fluorescence was followed over time. Fermentation of the carbohydrates led to the formation of acid in the medium. The increase of the acidity of the broth associated with carbohydrate utilization caused the blue pH indicator to become yellow. This lead to an unquenching and a dramatic rise in fluorescence of SR101 (FIGS. 12 and 13, mannose curves). The lack of utilization of the carbohydrate by the organism under test resulted in no color or fluorescence change (FIG. 13 trehalose and mannitol and FIG. 14). This differential utilization of the carbohydrates by the 3 species tested would form the basis of the ID system to differentiate the organisms. Therefore a battery of tests can be established in which the growth media will contain key ingredients that either can or cannot be utilized by a certain type of bacteria. The combination of these positive or negative results can serve as the basis of a simple identification scheme with results available in a rapid time frame (approximately seven hours at these inoculum levels). Similarly, inhibitors can be added to the medium which prevents the growth of certain bacteria but not others. For example, salt (NaCl) can be added to the medium and can effect the growth of certain bacteria.

The above examples illustrate the utility of the present invention as used for microbial detection, enumeration, identification, and antimicrobial susceptibility testing.

The present invention further provides advantages over prior art colorametric assays. The present invention can utilize a single optical window with no requirement for a second (epifluorescence), simple instrumentation (a lamp and a light detector and possibly filters to improve sensitivity), customer familiarity and acceptance with fluorescent methods, and proven utility. Fluorescence measurements can be made rapidly, by definition, in the millisecond time frame.

Further, fluorescence is non-invasive such that there is no requirement to physically enter a well containing the test sample at each reading. This eliminates contamination of the instrument and the cuvette containing the test sample.

The dye pair technology used in accordance with the present invention allows the use of reduction oxidation potentials, pH, and cleavage reactions as well as other reactions caused by diverse enzyme systems with a simple single wavelength instrument. There is no need to change filters or wavelengths to follow these reactions, as long as they create or reduce quenching of the analytical dye.

The present invention provides a rapid microbial identification and susceptibility test. Antimicrobial susceptibility patterns can be discerned as early as 2.5 hours, more typically from 4 to 9 hours, using $10^6$ cfu/ml inoculum. Using an inoculum level of $10^7$ cfu/ml, some identification reactions can be read from 1 to 2 hours after inoculation. This is a significant advantage over much slower prior art systems.

The present technology made and processed in accordance with the present invention is automatable. By merely reading the cuvette automatically by instrument at intervals, rather than manually loading a machine, total automation of the analysis can be accomplished. A computer can be programed to predict the identification and antimicrobial susceptibility results derived from the reaction progress curves.

By having a visible wavelength color reaction as an integral part of the analysis, the user can perform a manual backup of the system in case of instrument failure. In accordance with this aspect of the invention, the user would merely read the color changes evident, rather than the fluorescence by the machine, and interpret the results as described in a written code book.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A process for detecting microbial metabolism, said process including the steps of: combining a sample solution to be analyzed for metabolizing microorganisms, microbial growth medium, a nontoxic concentration of a first dye having an absorbance spectrum which in the presence of growing microorganisms changes in response to by products of metabolism released by the microorganism into the medium, and a nontoxic concentration of a second dye having an excitation or emission spectrum which overlaps with one of the changed or unchanged absorbance spectra of the first dye, neither dye being metabolized directly by the microorganisms; and observing either no change in the intensity of fluroescence emission of the second dye indicating the absence of metabolizing microorganisms in the sample or a change in the intensity of the fluorescence emission indicating the presence of metabolizing microorganisms in the sample.

2. A process as set forth in claim 1 wherein said combining step is further defined as changing the physical-chemical environment of the first dye as the microorganisms metabolize nutrients from the medium, and shifting the absorbance spectrum of the first dye, thus quenching or unquenching the emission spectrum of the second dye, said observing step being further defined as observing the quenching or unquenching of the second dye indicating the presence or absence of metabolizing microorganism.

3. A process as set forth in claim 2 wherein the growth medium contains specific nutrients which change the physical-chemical properties of the medium when metabolized by specific microorganisms, said changing step being further defined as changing the physical-chemical environment of the first dye as only a specific type of microorganism metabolizes the specific nutrient in the medium and observing the change in emission of the second dye as an identification of the presence of the specific type of microorganism.

4. A process as set forth in claim 3 further including the steps of repeating said combining step for several different media containing different specific nutrients, observing the changes or absence of changes of the emission spectrum of the second dye, and constructing an identification finger print of specific microorganisms based on the several observations.

5. A process as set forth in claim 2 wherein said changing step is further defined as changing the pH of the solution, the first dye having an absorbance spectrum which changes in response to the change in pH of the environment.

6. A process as set forth in claim 5 wherein said changing step is further defined as adding specific carbohydrates which are fermented to acidic end products by certain microorganisms thus changing the pH of the medium 7. A process as set forth in claim 5 wherein said changing step is further defined as adding urea which is enzymatically transformed by microorganisms containing urease and cleaved to ammonia and carbon dioxide and changing thus the pH of the environment.

8. A process as set forth in claim 2 wherein said changing step is further defined as growing the microorganisms and changing the reduction-oxidation potential of the environment, the first dye having an absorbance spectrum which changes in response to changes in reduction-oxidation potentials.

9. A process as set forth in claims 5 or 8 wherein the environment is intracellular.

10. A process as set forth in claims 5 or 8 wherein the environment is extracellular.

11. A process as set forth in claim 1 wherein said combining step is further defined as adding different antibiotics and/or growth inhibitor to different samples of the medium containing the microorganisms, said observing step being further defined observing which antibiotics and/or inhibitors prevent a change in the fluorescence emission of the second dye as indicating sensitivity or resistance of a microorganism to different antibiotics and/or inhibitors.

12. A process as set forth in claim 1 further including the step of incubating the combined medium and dyes at 30° to 35° C. for 2 to 8 hours while monitoring the changes in fluorescence.

13. A process as set forth in claim 1 wherein said combining step is further defined as adding 5 to 30 micromolar concentrations of the first dye and 2 to 20 micromolar concentrations of the second dye.

14. A kit for detecting microbial metabolism, said kit comprising: microbial growth medium; a nontoxic concentration of a first dye having an absorbance spectrum which in the presence of microorganisms changes in response to metabolism of the microorganism; a nontoxic concentration of a second dye having an exciation or emission spectrum which overlaps with one of the unchanged or changed absorbance spectrum of the first dye whereby addition of the first and second dyes to the medium without metabolizing microorganisms causes no change in the observed fluorescence emission of said second dye and with metabolizing microorganisms causes changes in the observed fluroescence emission of said second dye.

15. A kit as set forth in claim 14 wherein said first dye has an absorbance spectrum that changes in response to physical-chemical changes in the environment.

16. A kit as set forth in claim 15 wherein said first dye has an absorbance spectrum that changes in response to changes in pH of the environment.

17. A kit as set forth in claim 15 wherein said first dye has an absorbance spectrum that changes in response to reduction-oxidation potential of the environment.

18. A kit as set forth in claim 14 wherein said first dye has an absorbance spectrum, that changes when said first dye is metabolized by specific microorganisms.

* * * * *